(12) United States Patent
Marciano et al.

(10) Patent No.: US 12,409,332 B2
(45) Date of Patent: Sep. 9, 2025

(54) METHODS AND APPARATUSES FOR DELIVERING TUMOR TREATING FIELDS TO A SUBJECT'S BODY FOR NEAR-SURFACE TUMORS

(71) Applicant: Novocure GmbH, Root (CH)

(72) Inventors: Tal Marciano, Haifa (IL); Smadar Arvatz, Haifa (IL); Boaz Marsault, Haifa (IL)

(73) Assignee: Novocure GmbH, Baar (CH)

( * ) Notice: Subject to any disclaimer, the term of this patent is extended or adjusted under 35 U.S.C. 154(b) by 539 days.

(21) Appl. No.: 17/886,371

(22) Filed: Aug. 11, 2022

(65) Prior Publication Data

US 2023/0052780 A1 Feb. 16, 2023

Related U.S. Application Data

(63) Continuation of application No. 17/698,457, filed on Mar. 18, 2022.

(60) Provisional application No. 63/232,294, filed on Aug. 12, 2021, provisional application No. 63/232,329, filed on Aug. 12, 2021.

(51) Int. Cl.
*A61N 1/40* (2006.01)
*A61N 1/36* (2006.01)

(52) U.S. Cl.
CPC ........... *A61N 1/40* (2013.01); *A61N 1/36002* (2017.08)

(58) Field of Classification Search
None
See application file for complete search history.

(56) References Cited

U.S. PATENT DOCUMENTS

| 7,565,205 B2 | 7/2009 | Palti |
| 2019/0133673 A1 | 5/2019 | Boll et al. |
| 2020/0171297 A1 | 6/2020 | Kirson et al. |
| 2021/0162228 A1* | 6/2021 | Urman ..................... A61N 1/40 |
| 2022/0305276 A1 | 9/2022 | Marciano et al. |

* cited by examiner

*Primary Examiner* — Michael W Kahelin
(74) *Attorney, Agent, or Firm* — McCarter & English, LLP; Michael A. Sartori

(57) ABSTRACT

A method for determining a location of a transducer on a subject's body for applying tumor treating fields. The method comprises determining a near-surface portion of a tumor in the subject's body, the near-surface portion of the tumor closer to a surface of the subject's body than other portions of the tumor; determining a near-tumor position on the subject's body, the near-tumor position on the subject's body closer to the near-surface portion of the tumor than other positions of the subject's body; determining an outer perimeter of the transducer, the transducer comprising a plurality of electrode elements electrically coupled to each other, the plurality of electrode elements of the transducer being located within the outer perimeter; and identifying a portion of the outer perimeter of the transducer to be located substantially at the near-tumor position on the subject's body.

18 Claims, 7 Drawing Sheets
(2 of 7 Drawing Sheet(s) Filed in Color)

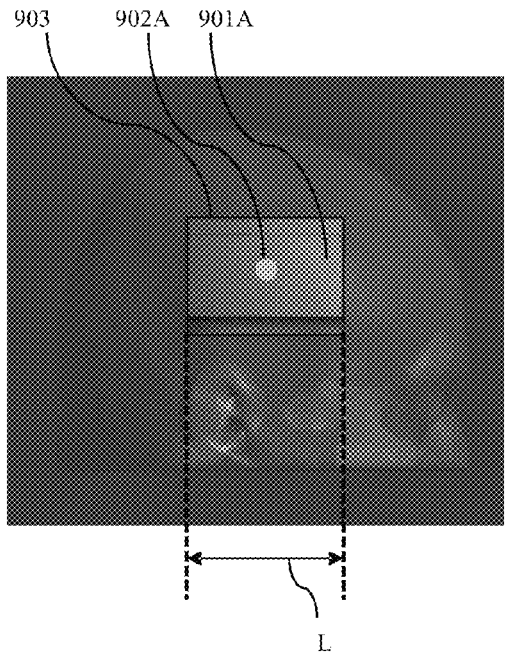
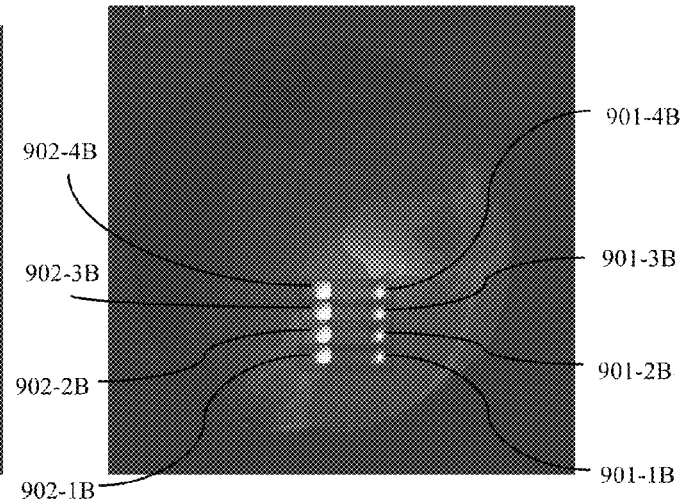
FIG. 9A
FIG. 9B
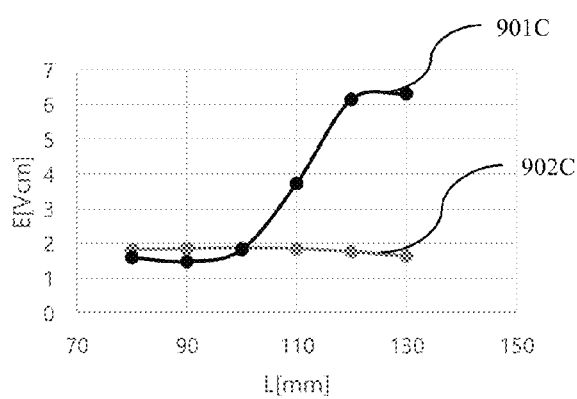
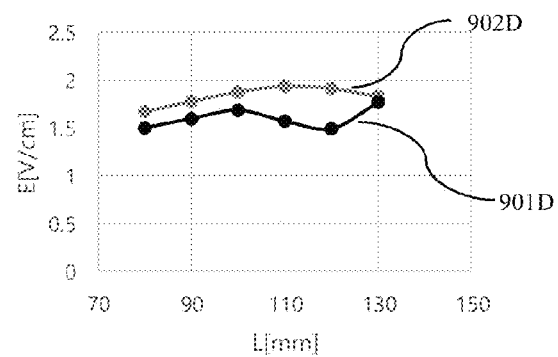
FIG. 9C
FIG. 9D

METHODS AND APPARATUSES FOR DELIVERING TUMOR TREATING FIELDS TO A SUBJECT'S BODY FOR NEAR-SURFACE TUMORS

CROSS-REFERENCE TO RELATED APPLICATIONS

This application claims priority to U.S. patent application Ser. No. 17/698,457 filed Mar. 18, 2022, U.S. Patent Application No. 63/232,329 filed Aug. 12, 2021, and U.S. Patent Application No. 63/232,294 filed Aug. 12, 2021, all of which are incorporated herein by reference.

BACKGROUND

Tumor treating fields (TTFields) are low intensity (e.g., 1-4 V/cm) alternating electric fields within the intermediate frequency range (e.g., 50 kHz to 1 MHz, such as 50-500 kHz), which may be used to treat tumors as described in U.S. Pat. No. 7,565,205. TTFields therapy is an approved monotreatment for recurrent glioblastoma (GBM) and an approved combination therapy with chemotherapy for newly diagnosed GBM patients. TTFields can also be used to treat tumors in other parts of a subject's body (e.g., lungs, ovaries, pancreas). For example, TTFields therapy is an approved combination therapy with chemotherapy for malignant pleural mesothelioma (MPM). TTFields are induced non-invasively into the region of interest by transducers (e.g., arrays of capacitively coupled electrode elements) placed directly on the patient's body (e.g., using the Novocure Optune™ system), and applying AC voltages between the transducers.

In the context of GBM, the conventional approach for positioning the transducers is to position the first pair of transducers on the front and back of the head, and to position the second pair of transducers on the right and left sides of the head. In the context of treating mesothelioma, a conventional approach for positioning the transducers is to position the first pair of transducers on the front and back of the torso, and to position the second pair of transducers on the right and left sides of the torso. An AC voltage generator applies an AC voltage (e.g., 200 kHz in the context of GBM or 150 kHz in the context of mesothelioma) between the first pair of transducers for a first interval of time (e.g., one second), which generates an electric field with field lines that generally run in the front-back direction. Then, the AC voltage generator applies an AC voltage at the same frequency between the second pair of transducers for a second interval of time (e.g., one second), which generates an electric field with field lines that generally run in the right-left direction. The system then repeats this two-step sequence for the duration of the treatment.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 9A-9F depict example simulation results of electric field strength delivered to tumors as a function of the length of the transducer, in each case comparing the positioning of the transducer (a) such that the tumor is located centrally within the transducer array perimeter with (b) that of positioning the transducer such that the tumor is located at the edge of the transducer array perimeter. Each of FIGS. 9C-9F represent the relationship for different distances to the surface of the subject's head, with FIG. 9C showing the closest distance to the surface of the subject's head.

Various embodiments are described in detail below with reference to the accompanying drawings, wherein like reference numerals represent like elements.

DESCRIPTION OF EMBODIMENTS

Figure 1:
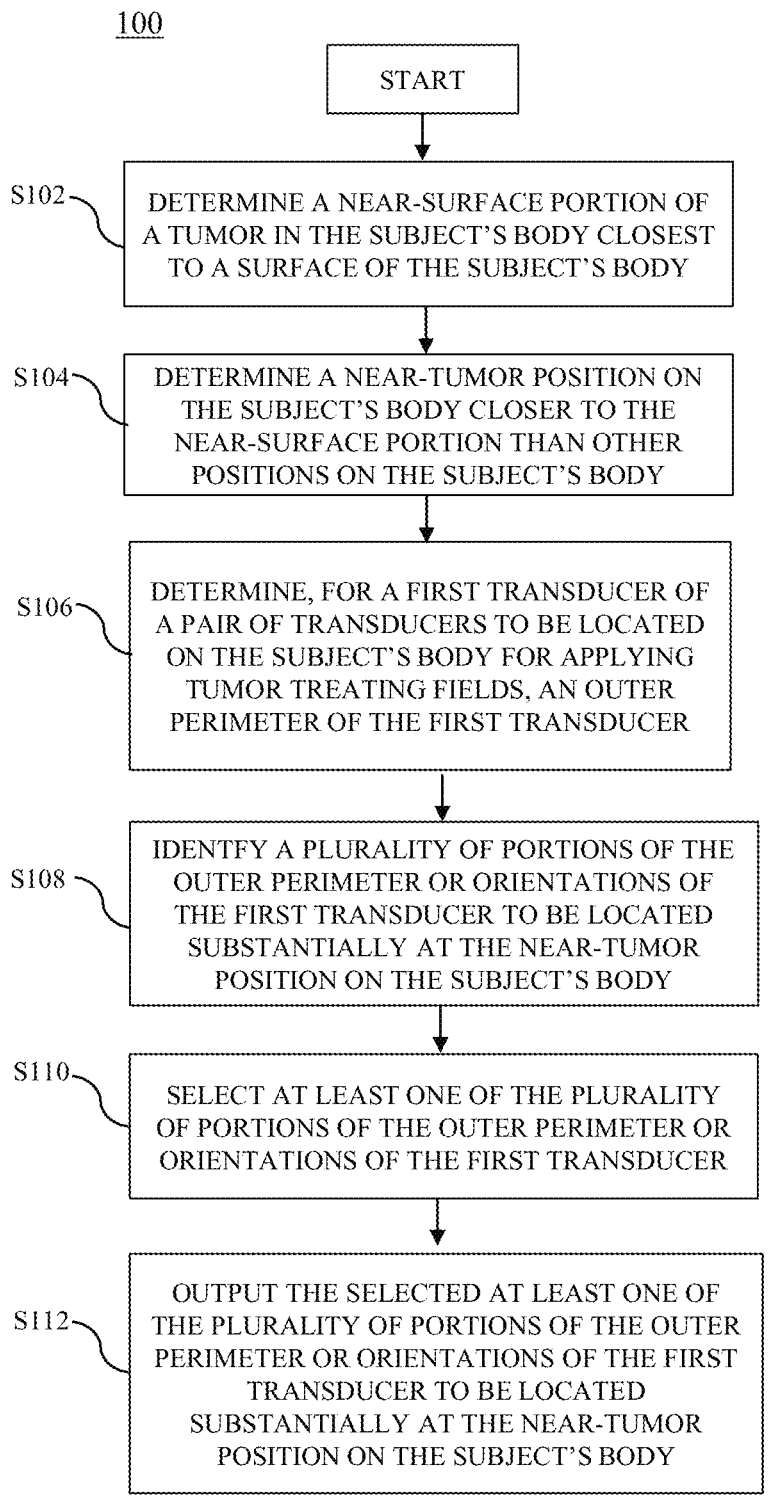
FIG. 1 is a flowchart depicting an example of determining a location of a transducer on a subject's body for applying TTFields.

To provide a subject with an effective tumor treating fields (TTFields) treatment, the precise locations at which to place the transducers on the subject's body to deliver high electric field strength to a target tumor must be generated. In order to determine these transducer locations, one or more near-tumor positions on the subject's body closer to at least a portion of the tumor than other positions of the subject's body are determined. Next, transducer locations on the subject's body are typically determined with a central portion or a near central portion of the transducers located at the one or more near-tumor positions.

The inventors discovered that, on a transducer comprising an array of electrode elements, the electrode elements located along the edge of the array may have a lower resistance to current flowing therethrough compared to the electrode elements located toward the middle of the array. This can lead to higher concentrations of electric charge at points on the edge (e.g., outer perimeter) of the array in general. Further, an electrode element located at a corner or similar sharp bend in the edge of the array will have a higher concentration than other electrode elements along the edge and in the center of the array. The tendency of a transducer to drive higher amounts of current through electrode elements located along the edge of the array, and particularly at the corners, is referred to herein as the "edge effect."

Having recognized this problem, the inventors discovered an approach to apply TTFields by placing the edge (e.g., outer perimeter) of the transducer at the near-tumor position on the subject's body. By placing the outer perimeter of the transducer at the near-tumor position, the edge effect of the transducer may be utilized, and thus increased electric field strength may be delivered to target tumor sites, thereby positively influencing the therapeutic effect of the TTFields.

The present invention can be understood more readily by reference to the following detailed description, examples, drawings, and claims, and their previous and following description. However, it is to be understood that this invention is not limited to the specific apparatuses, devices, systems, and/or methods disclosed unless otherwise specified, and as such, of course, can vary.

Headings are provided for convenience only and are not to be construed to limit the invention in any manner. Embodiments illustrated under any heading or in any portion of the disclosure may be combined with embodiments illustrated under the same or any other heading or other portion of the disclosure.

Any combination of the elements described herein in all possible variations thereof is encompassed by the invention unless otherwise indicated herein or otherwise clearly contradicted by context.

Some or all of the embodiments disclosed herein may refer to the location of transducers on the body for treatment of tumors located in the body. Some or all of the embodiments disclosed herein may refer to the location of transducers on the head for treatment of tumors located in the head, such as, for example, in the brain. Some or all of the embodiments disclosed herein may refer to the location of transducers on the torso or other parts of the body for treatment of tumors located in the torso or other parts of the body.

As used in the specification and the appended claims, the singular forms "a," "an" and "the" include plural referents unless the context clearly dictates otherwise.

FIG. 1 depicts a flowchart depicting an example method 100 of determining a location of a transducer on a subject's body for applying TTFields. In this example, an electric field is applied between one pair of transducers. However, it should be noted that the method 100 applies similarly for each electric field when two electric fields are applied between two pairs of transducers. Each pair of transducers corresponds to a channel for generating TTFields in the subject's body.

Certain steps of the method 100 are described as computer-implemented steps. The computer may be any device comprising one or more processors and memory accessible by the one or more processors, the memory storing instructions that when executed by the one or more processors cause the computer to perform the relevant steps of the method 100.

With reference to FIG. 1, at step S102, the method 100 comprises determining a near-surface portion of a tumor in the subject's body closest to a surface of the subject's body. The determination of the near-surface portion of a tumor is based on, for example, the location of the tumor in the subject's body, the size and shape of the tumor, and the type of the tumor. In one example, the near-surface portion of the tumor is determined by image data. The image data may comprise one or more images of a portion of the subject's body. The image data may, for example, comprise one or more X-ray images, magnetic resonance imaging (MRI), computerized tomography (CT) images, ultrasound images, or any image of the subject's body providing an internal view of the subject's body. Each image may include an outer shape of a portion of the subject's body, and a region corresponding to a tumor within the subject's body. In one embodiment, one or more near-surface portions of the tumor may be determined. In one example, the one or more near-surface portions of the tumor may be ranked based on their distance to the surface of the subject's body.

At step S104, the method 100 comprises determining a near-tumor position on the subject's body closer to the near-surface portion of the tumor than other positions of the subject's body. In one example, the determination of the near-tumor position on the subject's body is based on image data, e.g., one or more X-ray images, MRI, CT, ultrasound images, any image of the subject's body providing an internal view of the subject's body. Each image may include an outer shape of a portion of the subject's body and a region corresponding to a tumor within the subject's body.

In some embodiments, the tumor is located near the surface of the subject's body. In one embodiment, for example, the near-surface portion of the tumor is less than or equal to 80 mm from the near-tumor position on the subject's body. As another example, the near-surface portion of the tumor is less than or equal to 66 mm from the near-tumor position on the subject's body. In other embodiments, the near-surface portion of the tumor is less than or equal to 100, 90, 80, 70, 66, 60, 50, 40, 30 mm, or even less than 20 mm from the near-tumor position on the subject's body. In another embodiment, for example, when drawing a line segment intersecting the near-surface portion of the tumor wherein the line segment having first and second end points on opposite sides of the subject's body and the first end point intersecting the near-tumor position on the subject's body, the distance between the first end point and the near-surface portion of the tumor is equal to or less than 50% of a distance between the second end point and the near-surface portion of the tumor. As another example, the distance between the first end point and the near-surface portion of the tumor is equal to or less than 25% of the distance between the second end point and the near-surface portion of the tumor. In other embodiments, the distance between the first end point and the near-surface portion of the tumor is equal to or less than 50%, 40%, 30%, 25%, 20%, or, even, less than 10% of the distance between the second end point and the near-surface portion of the tumor.

Figure 6A:
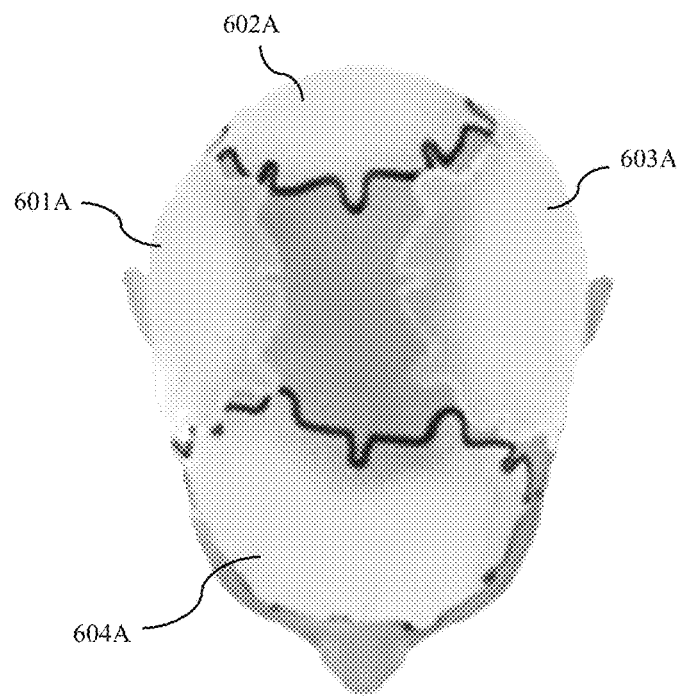
FIGS. 6A and 6B depict examples of attaching transducers to the subject's body for delivering tumor treating fields.
Figure 6B:
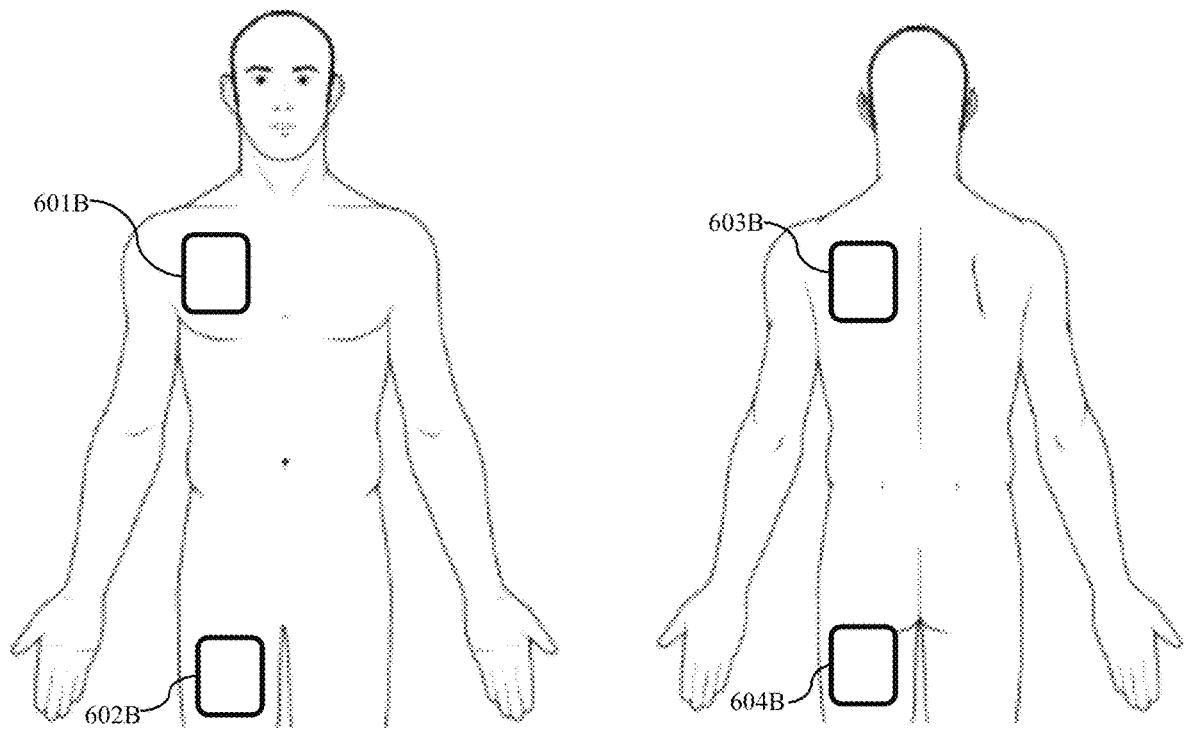

In one example, the location of the tumor is in the head of the subject's body. In this example, the near-tumor position is on the surface of the subject's head. For example, the near-tumor position may be located on the skull. In another example, the location of the tumor is in the torso of the subject's body. In this example, the near-tumor position is on the surface of the subject's torse. For example, the near-tumor position is on the chest, back, or abdomen of the subject's body. Examples of transducers for use with the head and torso are illustrated in FIGS. 6A-6B, which are discussed further below.

At step S106, the method comprises determining, for a first transducer of a first pair of transducers to be located on the subject's body for applying TTFields, an outer perimeter of the first transducer. In one example, the first transducer includes a plurality of electrode elements electrically coupled to each other, and the plurality of electrode elements of the first transducer are located within the outer perimeter. In one example, the outer perimeter of the first transducer is substantially square, rectangular, regular polygonal, irregular polygon, circular, oval, ovaloid, ovoid, or elliptical in shape. In present embodiments, substantially square, rectangular, regular polygonal, or irregular polygonal outer perimeters include substantially square, rectangular, regular polygonal, or irregular polygonal shapes with rounded vertices. In one example, a surface area of the first transducer is equal to or greater than 5000 mm$^2$. As another example, the surface area of the first transducer is equal to or greater than 6500 mm$^2$. In other embodiments, the surface area of the first transducer is equal to or greater than 1000, 2000, 3000, 4000, 5000, 6000, 6500, 7000, 8000 9000, 10000, 15000 20000, 25000, or 50000, or 75000 mm$^2$. Generally, the surface area of the first transducer is less than or equal to 75000 mm$^2$ (750 cm$^2$), although the maximum surface area is dependent on the size of the person (or animal) to be treated. For example, the surface area of the first transducer may be from 1000 to 75000 mm², or from 2000 to 60000 mm², or from 4000 to 50000 mm², or from 4000 to 25000 mm².

In one embodiment, the outer perimeter of the first transducer is an edge of the first transducer. In another embodiment, the outer perimeter of the first transducer is a convex periphery of the first transducer. In one example, the convex periphery surrounds all of the electrode elements of the first transducer. In another example, the convex periphery touches at least three of the electrode elements.

In one example, the portion of the outer perimeter of the first transducer to be located substantially at the near-tumor position on the subject's body touches at least one of the electrode elements of the first transducer. In other embodiments, the portion of the outer perimeter of the first transducer to be located substantially at the near-tumor position on the subject's body touches at least two, or at least three, of the electrode elements of the first transducer. In another example, the portion of the outer perimeter of the first transducer to be located substantially at the near-tumor position on the subject's body is 20% or less of the outer perimeter. As another example, the portion of the outer perimeter of the first transducer to be located substantially at the near-tumor position on the subject's body is 10% or less, or, even, 5% or less of the outer perimeter.

In one embodiment, the first transducer is configured to be positioned over the subject's body with a face of the first transducer facing the subject's body. In one example, when viewed from the direction perpendicular to the face of the first transducer, a number of the electrode elements of the first transducer are peripheral electrode elements defining the outer perimeter of the first transducer, and the peripheral electrode elements substantially surround any other electrode elements of the first transducer. In another example, when viewed from a direction perpendicular to the face of the first transducer, the near-surface portion of the tumor is substantially within the outer perimeter of the first transducer.

In one embodiment, the electrode elements of the first transducer are capacitively coupled. In another embodiment, the electrode elements of the first transducer are not capacitively coupled. In one embodiment, the electrode elements of the first transducer comprise ceramic disks. In one example, each of the ceramic disks is approximately 2 cm in diameter and approximately 1 mm in thickness at the largest thickness. In other embodiments, the electrode elements of the first transducer are ceramic elements that are not disk-shaped. In another embodiment, the electrode elements of the first transducer are non-ceramic dielectric material. Examples of a non-ceramic dielectric material include polymer films. Examples of these embodiments are illustrated in FIGS. 4A-4B and 5A-5B, which are discussed further below.

The power density of the TTField may be used to represent the TTField dose delivered to the tumor. The power density of the applied TTField may be in terms of, for example, Watts/volume. In one example, the power density of the applied TTField may be in units of, for example, mW/cm³. The power density of the applied TTField between the first transducer and the second transducer may be calculated by the following equation:

$$P = \tfrac{1}{2}\sigma E^2 \qquad \text{Equation 1}$$

where P is the power density of the applied TTField; σ is the conductivity of tissue; and E is the magnitude of the electric field of the applied TTField.

As discussed above, on a transducer comprising an array of electrode elements, the electrode elements located along the edge of the array may drive higher amounts of current compared to the electrode elements located toward the center of the array (e.g., edge effect). Therefore, according to Equation 1, the power density along the edge of the transducer may be higher than the central portion of the transducer. In one embodiment, the power density at the outer perimeter of the transducer may be 100% to 300% of the power density of the central portion of the transducer. For example, the power density at the outer perimeter of the transducer may range from as low as 100, 110, 120, 130, 140, 150, 160, 170, 180, 190, or 200% of the power density of the central portion of the transducer; and as high as 150, 160, 170, 180, 190, 200, 210, 220, 230, 240, 250, 260, 270, 280, 290, or 300% of the power density of the central portion of the transducer; such as, for example, 120-280% or 150-250% of the power density of the central portion of the transducer.

Hence, when a tumor is near a surface of the subject's body, that is, the tumor is located close to the first transducer, placing the edge, rather than the central portion, of the first transducer at the near-tumor position on the subject's body may deliver higher electric field power to the tumor because the power density at the edge is higher than the power density at the central portion of the transducer. When the tumor is located far from the surface of the subject's body, that is, the tumor is located far from the first transducer, placing the central portion or the near central portion rather than the edge of the first transducer at the near-tumor position on the subject's body may deliver higher electric field power to the tumor because the accumulated electric field power of the edge and the central portion of the transducer may be delivered to the tumor. Examples of these embodiments are simulated and illustrated in FIGS. 9A-9F, which are discussed further below.

At step S108, the method 100 comprises identifying a plurality of portions of the outer perimeter of the first transducer or a plurality of orientations of the first transducer to be located substantially at the near-tumor position on the subject's body. As an example, when the outer perimeter of the first transducer is substantially square, rectangular, regular polygonal, or irregular polygonal, the plurality of portions of the outer perimeter may include one or more corners (e.g., sharp or rounded vertices), and one or more edge of the substantially square, rectangle, regular polygon, or irregular polygon. As an example, when the outer perimeter of the first transducer is substantially circular, oval, ovaloid, ovoid, or elliptical in shape, the plurality of portions of the outer perimeter may include arcs or perimeter portions of the substantially circle, oval, ovaloid, ovoid, or ellipse.

At step S110, the method comprises selecting at least one of the plurality of portions of the outer perimeter or at least one of the plurality of orientations of the first transducer. In one example, the selection of the at least one of the plurality of portions of the outer perimeter of the first transducer are based on the shape of the outer perimeter, the distribution of the electrode elements on the outer perimeter, and/or the size and shape of the tumor. As an example, when the outer perimeter of the first transducer is substantially square, rectangular, regular polygonal, or irregular polygonal, at least one of the one or more corners (e.g., sharp or rounded vertices) may be selected. As an example, when the outer perimeter of the first transducer is substantially circular, oval, ovaloid, ovoid, or elliptical in shape, at least one or more of the arcs or perimeter portions may be selected. As another example, the selected at least one portion of the outer perimeter touches at least one of the electrode elements of the first transducer. In other embodiments, the selected at least one portion of the outer perimeter touches at least two, or at least three, of the electrode elements of the first transducer.

In one embodiment, the outer perimeter of the first transducer is the edge of the first transducer. In this example, the method may comprise identifying and outputting, a segment of the edge (e.g., outer perimeter) of the first transducer. When viewed from the direction perpendicular to a face of the first transducer to be positioned over the subject's body, the segment of the edge substantially overlaps the near-surface location of the tumor. In one example, the segment of the edge being closer to the near-surface location of the tumor than a centroid of the first transducer.

In another embodiment, the outer perimeter of the first transducer is the convex periphery of the first transducer. In this example, the method 100 may comprise identifying and outputting a near-tumor portion of the convex periphery of the first transducer to be located on the subject's body closer to the near-surface location of the tumor than other portions of the first transducer.

At step S112, the method 100 comprises outputting the selected at least one of the plurality of portions of the outer perimeter or at least one of the plurality of orientations of the first transducer at step S110 to be located substantially at the near-tumor position on the subject's body. In one embodiment, the at least one of the plurality of portions of the outer perimeter or at least one of the plurality of orientations of the first transducer is output on an output device.

Figure 2:
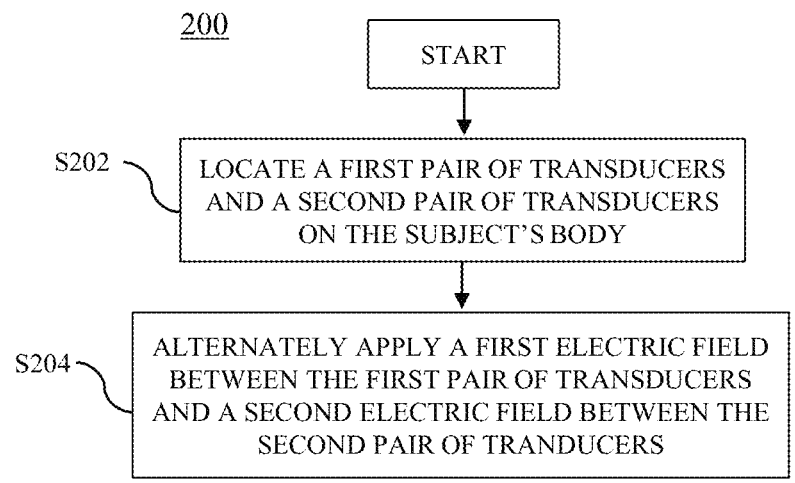
FIG. 2 is a flowchart depicting an example for applying TTFields to a subject's body having a tumor.

FIG. 2 depicts a flowchart depicting an example method 200 for applying TTFields to a subject's body having a tumor. In this example, two electric fields are alternately applied between two pairs of transducers.

Referring to FIG. 2, at step S202, the method 200 comprises locating a first pair of transducers and a second pair of transducers on the subject's body. In one example, the first pair of transducers includes a first transducer and a second transducer, and the second pair of transducers includes a first transducer and a second transducer. Each transducer of the first pair of transducers and the second pair of transducers may be a transducer having an array of electrode elements. In one example, a location to place at least one of the transducers of the first pair of transducers and second pair of transducers is determined according to the method 100.

In one example, the first and the second transducers of the first pair of transducers are capacitively coupled, and the first and the second transducers of the second pair of transducers are capacitively coupled. In another example, the first and the second transducers of the first pair of transducers are not capacitively coupled, and the first and second transducers of the second pair of transducers are not capacitively coupled.

In one example, the first pair of transducers and the second pair of transducers are located on the head of the subject's body. In another example, the first transducers of the first pair and the second pair of transducers are located on the head of the subject's body, and the second transducers of the first pair and second pair of transducer are located on the neck of the subject's body. In another example, the first pair and second pair of transducers are located on the torso of the subject's body. In another example, the first transducers of the first pair and second pair of transducers are located on the torso of the subject's body, and the second transducers of the first pair and second pair of transducers are located below the torso of the subject's body.

At step S202, the method 200 comprises alternately generating a first tumor treating electric field (TTField) between the first pair of transducers and a second tumor treating electric field (TTField) between the second pair of transducers. The first TTField is produced by applying a first AC voltage, generated by a first AC generator, between the first pair of transducers for a first time period and has, for example, a low intensity (e.g., 1-4 V/cm) and intermediate frequency range (e.g., 125-250 kHz, or in some cases, 50-500 kHz). In one example, the frequency of the first TTField is 150 kHz. The first AC voltage is applied to the first pair of transducers for the first time period (e.g., one second). After the first time period, the generation of the first TTField is ceased. Next, the second TTField is produced by applying a second AC voltage, generated by a second AC generator, between the second pair of transducers for a second time period and has, for example, a low intensity (e.g., 1-4 V/cm) and intermediate frequency range (e.g., 125-250 kHz, or in some cases, 50-500 kHz). In one example, the frequency of the second TTField is 150 kHz. The second AC voltage is applied to the second pair of transducers for the second time period (e.g., one second). The second time period and the first time period may be the same or different. After the second time period, the generation of the second TTField is ceased. Next, the method repeats the process of alternately generating the first TTFields between the first pair of transducers for the first time period and generating the second TTFields between the second pair of transducers for the second time period.

Figure 3:
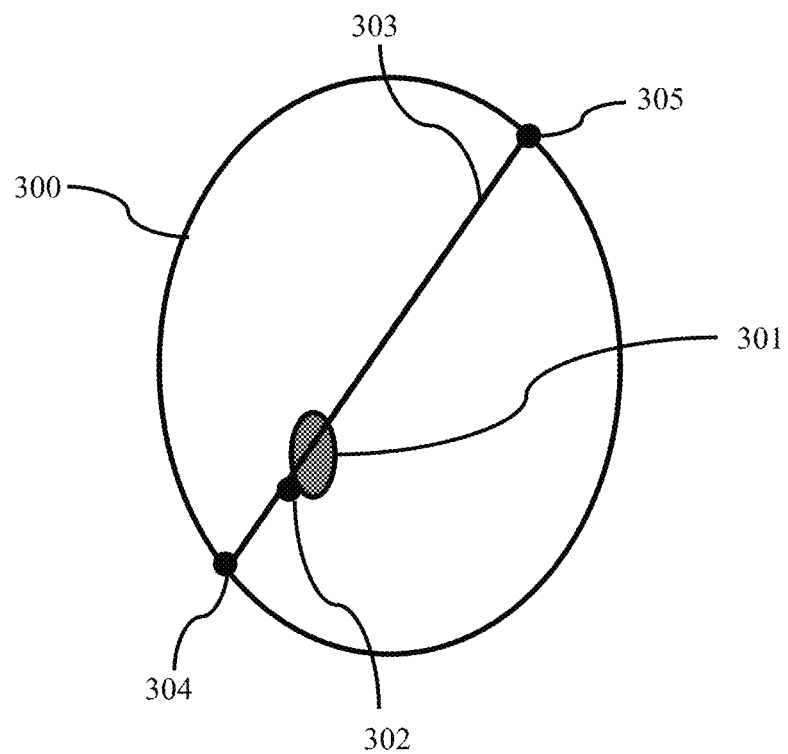
FIG. 3 depicts an example of determining a location of a transducer on a subject's body based on the location of a tumor for applying TTFields.

FIG. 3 depicts an example of determining a location of a transducer on a subject's body based on the location of a tumor for applying TTFields.

In the example depicted in FIG. 3, a tumor 301 is located in a subject's body 300. In this example, the tumor 301 is located in the subject's head. A near-surface portion 302 of the tumor 301 is determined. In one example, the near-surface portion 302 of the tumor 301 is closer to a surface of the subject's body than other portions of the tumor 301. A near-tumor position 304 on the subject's head is determined based on the near-surface portion 302. In one example, the near-tumor position 304 is closer to the near-surface portion 302 of the tumor 301 than other positions of the subject's body. A line segment 303 intersects the near-surface portion 302 and the near-tumor position 304. In one example, the line segment 303 has first and second end points on opposite sides of the subject's body. In this example, the first end point is the near-tumor position 304 and the second end point 305 is on the opposite side of the subject's head.

In one example, the distance between the near-surface portion 302 and the near-tumor position 304 is less than or equal to 80 mm. In another example, the distance between the near-surface portion 302 and the near-tumor position 304 is less than or equal to 66 mm. In other examples, the distance between the near-surface portion 302 and the near-tumor position 304 is less than or equal to: 80 mm, or 70 mm, or 66 mm, or 60 mm, or 55 mm, or 50 mm, or 45 mm, or 40 mm, or 35 mm, or, even, less than or equal to 30 mm, such as, for example, from 30-80 mm, or from 35-80 mm, or from 40-80 mm. In another example, the distance between the near-tumor position 304 and the near-surface portion 302 is equal to or less than 50% of the distance between the second end point 305 and the near-surface portion 302. In another example, the distance between the near-tumor position 304 and the near-surface portion 302 is equal to or less than 25% of the distance between the second end point 305 and the near-surface portion 302. In other embodiments, the distance between the near-tumor position 304 and the near-surface portion 302 is equal to or less than: 50%, 40%, 30%, 25%, 20%, 10% or, even, equal to or less than 5% of the distance between the second end point 305 and the near-surface portion 302. For example, the distance between the near-tumor position 304 and the near-surface portion 302 may be from 5% to 50%, or from 5% to 30% of the distance between the second end point 305 and the near-surface portion 302.

In one embodiment, a location of a first transducer of a first pair of transducers on the subject's body is determined based on the near-tumor position 304. As an example, the first transducer is located with a portion of an outer perimeter of the first transducer located substantially at the near-tumor position 304. In one embodiment, when viewed from the direction perpendicular to the face of the first transducer, the near-tumor position on the surface of the subject's body is located at a distance from the outer perimeter of the first transducer that is less 10%, or, even, less than 5%, such as from 0% to 5%, of the distance from the outer perimeter of the transducer to the centroid of the transducer. In another embodiment, when viewed from the direction perpendicular to the face of the first transducer, the near-tumor position on the surface of the subject's body is located at a distance from the outer perimeter of the first transducer that is less than 50%, less than 30%, less than 25%, less than 20%, less than 15%, less than 10%, or less than 5% of the distance from the outer perimeter of the transducer to the centroid of the transducer. In another embodiment, when viewed from the direction perpendicular to the face of the first transducer, the near-tumor position on the surface of the subject's body is located at a distance from the outer perimeter of the first transducer that is from 0% to 50%, or from 5% to 50%, or from 0% to 30%, or, even, from 5% to 30% of the distance from the outer perimeter of the transducer to the centroid of the transducer. In another embodiment, a location of a second transducer of the first pair of transducers on the subject's body is determined based on the second end point 305. In one example, the second transducer is located with a central portion of the second transducer located substantially at the second end point 305. One example of the first transducer and the second transducer are transducer arrays, each including a plurality of electrically coupled electrode elements.

Figure 4A:
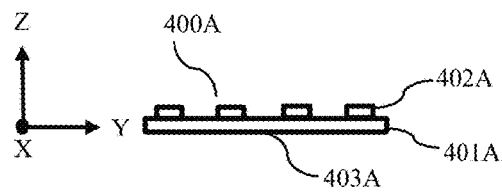
FIGS. 4A and 4B depict examples of the structure of transducers with a plurality of coupled electrode elements.
Figure 4B:
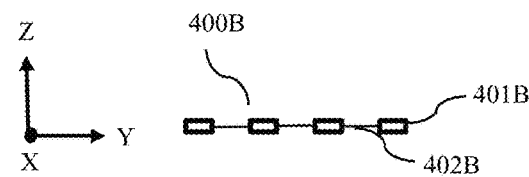

FIGS. 4A and 4B are examples of the structure of the transducer. For example, as shown in FIG. 4A, the transducer 400A has a substrate 401A and a plurality of electrode elements 402A. The substrate 401A is configured for attaching the transducer to a subject's body. Suitable materials for the substrate 401A should be, or contain, conductive materials and may include, for example, cloth, foam, and flexible plastic. In one example, the substrate 401A is or includes a conductive medical gel which may typically have a thickness of approximately 0.5 mm or more, or may be infused/absorbed in the substrate material (e.g., cloth, foam, flexible plastic, etc.). In another example, the substrate 401A is or includes a conductive adhesive which may have a thickness of approximately 20 μm or more, or may be infused/absorbed in the substrate material (e.g., cloth, foam, flexible plastic, etc.). In a more specific example, the substrate 401A is a layer of conductive hydrogel with a minimum thickness of 0.5 mm. In one example, the transducer 400A is configured to be positioned over the subject's body with a face of the transducer 403A facing the subject's body.

A plurality of capacitively coupled electrode elements 402A are positioned on the substrate 401A, and each of the capacitively coupled electrode elements has a conductive plate with a dielectric layer disposed thereon that faces towards the substrate. Optionally, one or more sensors may be positioned beneath each of the electrode elements in a manner that is similar to the conventional arrangement used in the Novocure Optune® system. In one example, the one or more sensors are temperature sensors (e.g., thermistors).

FIG. 4B depicts another example of the structure of the transducer 400B. In this example, the transducer 400B includes a plurality of electrode elements 401B. The plurality of electrode elements 401B are electrically and mechanically connected to one another without a substrate. In one example, the electrode elements 401B are connected to one another through conductive wires 402B.

Figure 5A:
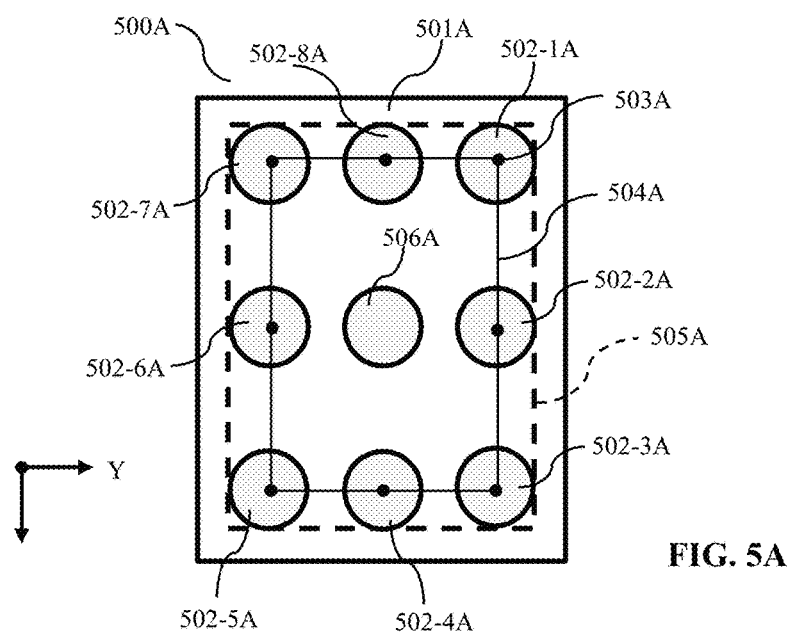
FIGS. 5A and 5B depict examples of the structure of transducers.
Figure 5B:
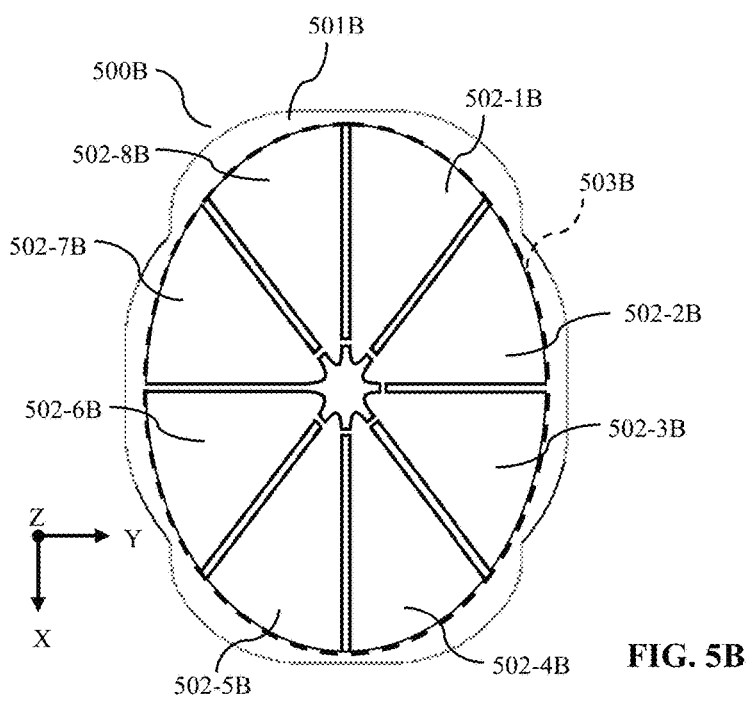

FIGS. 5A and 5B depict examples of the structure of a transducer with a plurality of electrically coupled electrode elements when viewed from a direction perpendicular to the face of the transducer facing the subject's body.

In the example depicted in FIG. 5A, the transducer 500A has a substrate 501A and a plurality of electrode elements 502A (e.g., 502-1A to 502-8A, and 506A). The substrate 501A is configured for attaching the transducer to a subject's body. Suitable materials for the substrate 501A include, for example, cloth, foam, and flexible plastic as discussed above.

A plurality of capacitively coupled electrode elements 502-A (e.g., 502-1A to 502-8A, and 506A) are positioned on the substrate 501A, and each of the capacitively coupled electrode elements 502-A has a conductive plate with a dielectric layer disposed on the substrate. Optionally, one or more sensors may be positioned beneath each of the electrode elements in a manner that is similar to the conventional arrangement used in the Novocure Optune® system. In one example, the one or more sensors are temperature sensors (e.g., thermistors).

In some embodiments, a number of the electrode elements 502-1A to 502-8A of the transducer 500A define an outer perimeter of the transducer. In one example, the outer perimeter 504A of the transducer 500A is determined by the centroids 503A of the electrode elements of the outer perimeter. In this example, the centroid of the peripheral electrode elements 502-1A to 502-8A define the outer perimeter 504A. In this example, the outer perimeter 504A is rectangular.

In another example, the outer perimeter 505A of the transducer 500A is determined by a shape enclosing and touching a number of the electrode elements of the outer perimeter. In this example, the outermost edge of the peripheral electrode elements 502-1A to 502-8A define the outer perimeter 505A.

In one example, the peripheral electrode elements 502-1A to 502-8A surround other electrode elements (e.g., electrode element 506A located in the center of the transducer 500A).

In one embodiment, when locating the outer perimeter of the transducer 500A substantially at the near-tumor position on the subject's body, at least one of the peripheral electrode elements 502-1A to 502-8A is located substantially at the near-tumor position.

FIG. 5B depicts an example of the transducer 500B with non-ceramic electrically coupled electrode elements 502-B (e.g., 502-1B to 502-8B). In this example, the transducer 500B has a substrate 501B and a plurality of non-ceramic electrode elements 502-B (e.g., 502-1B to 502-8B). In one embodiment, the non-ceramic electrode elements include a flexible dielectric material. Examples of flexible dielectric materials include dielectric polymers or dielectric co-polymers. In some embodiments, the non-ceramic electrode elements 502-1B to 502-8B are non-circular shaped. In this example, the electrode elements 502-1B to 502-8B are substantially triangular or wedge shaped. In another embodiment, the transducer 500B does not include a substrate. In this example, the non-ceramic electrode elements electrode elements 502-1B to 502-8B are directly attached to the subject's body.

In some embodiments, a number of the electrode elements 502-1B to 502-8B define an outer perimeter of the transducer 500B. In the example depicted in FIG. 5B, the outer perimeter 503B of the transducer 500B is oval shaped. In this example, the outermost edge of the peripheral electrode elements 502-1B to 502-8B define the outer perimeter 503B.

Transducers that use an array of electrode elements that are not capacitively coupled may also be used. In this situation, the transducers 500A and 500B may be implemented using a region of a conductive material that is configured for placement against a subject's body, with no insulating dielectric layer disposed between the conductive elements and the body.

FIGS. 6A and 6B depict examples of attaching the transducers to the subject's body for delivering tumor treating fields.

In the example depicted in FIG. 6A, transducers 601A, 602A, 603A, and 604A are attached to a subject's head for applying TTFields to the subject's head. In one embodiment, two electric fields are alternately applied between two pairs of transducers. Each pair of transducers corresponds to a channel for generating TTFields in the subject's body. As for pairs of transducers, the transducer 601A and 603A may form a first pair of transducers, and the transducer 602A and 604A may form a second pair of transducers.

In the example depicted in FIG. 6B, transducers 601B, 602B, 603B, and 604B are attached to a subject's body for applying TTFields to the subject's torso. In one embodiment, two electric fields are alternately applied between two pairs of transducers. Each pair of transducers corresponds to a channel for generating TTFields in the subject's body. In the example depicted in FIG. 6B, transducer 601B is attached to the front of the subject's right chest, transducer 602B is attached to the front of subject's right thigh, transducer 603B is attached to the back of the subject's left chest, and transducer 604B is attached to the back of the subject's left thigh. As for pairs of transducers, the transducers 601B and 604B may form a first pair of transducers, and the transducers 602B and 603B may form a second pair of transducers.

Figure 7A:
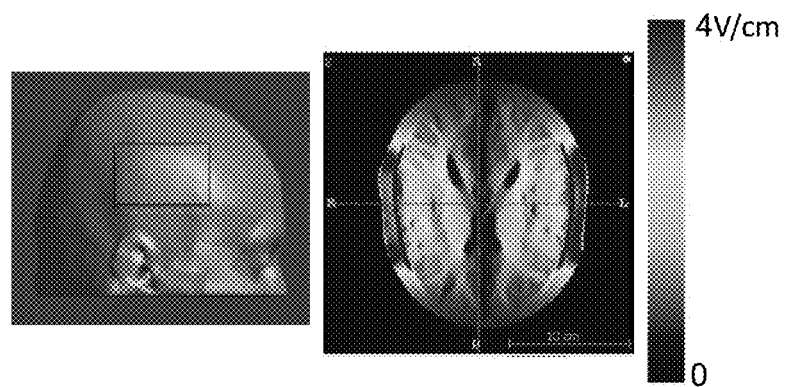
FIGS. 7A and 7B depict example simulation results of electric field strength when electric fields are applied through transducers of different sizes to a subject's head.
Figure 7B:
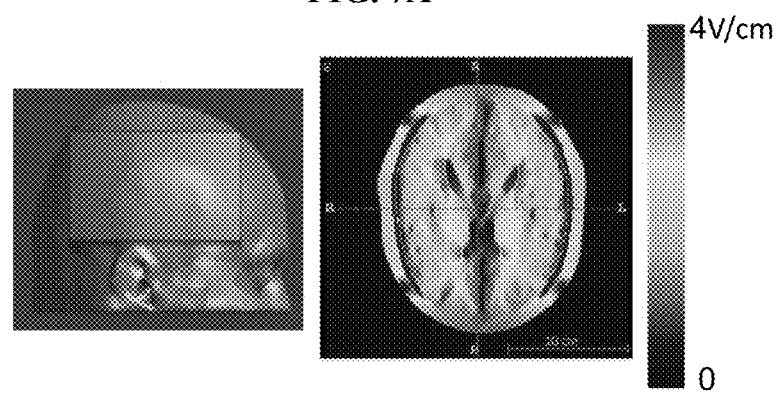

FIGS. 7A and 7B depict example simulation results of electric field strength when electric fields are applied through transducers of different sizes to a subject's head. In the example depicted in FIGS. 7A and 7B, the transducers are conductive flexible sheets. In addition, the same TTFields with the same frequency and voltage are used to obtain the simulation results shown in FIGS. 7A and 7B.

FIG. 7A includes an image of the side view of a three-dimensional model of a subject's head and a horizontal slice through the head of the three-dimensional model showing the distribution of the field strength through the three-dimensional model. In this example, a rectangle shaped transducer of a size of 80×52 mm$^2$ is simulated to deliver the TTFields to the subject's head. In this example, a surface area of the rectangle transducer is 4,160 mm$^2$. As shown in the horizontal slice through the head in FIG. 7A, the field strength near the surface of the head is approximately 3.5 V/cm (orange/red in color), and the field strength is substantially evenly distributed along the length of the transducer. As such, the simulation result in FIG. 7A does not exhibit an edge effect.

FIG. 7B includes an image of the side view of a three-dimensional model of a subject's head and a horizontal slice through the head of the three-dimensional model showing the distribution of the field strength through the three-dimensional model. In this example, a rectangle shaped transducer with a size of 140×91 mm$^2$ is simulated to deliver a TTFields to the subject's head. In this example, a surface area of the rectangle transducer is 12,740 mm$^2$. As shown in the horizontal slice through the head in FIG. 7B, the field strength near the surface of the head at the points of the edges of the transducer is approximately 3.5 V/cm (orange/red in color), and the field strength near the surface of the head between the two edges of the transducer is approximately 2 V/cm (yellow/green in color). As such, the simulation result in FIG. 7B exhibits an edge effect.

Figures 8A, 8B:
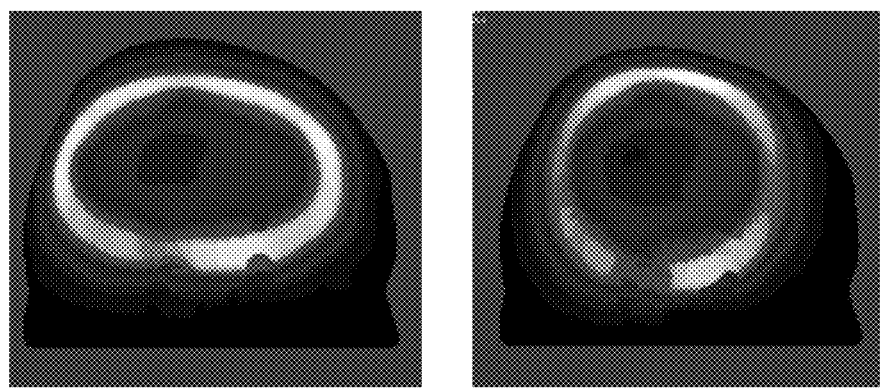
FIGS. 8A-8C depict example simulation results of electric power absorbed by the tissue when electric fields are applied through transducers of different shapes to a subject's head.
Figure 8C:
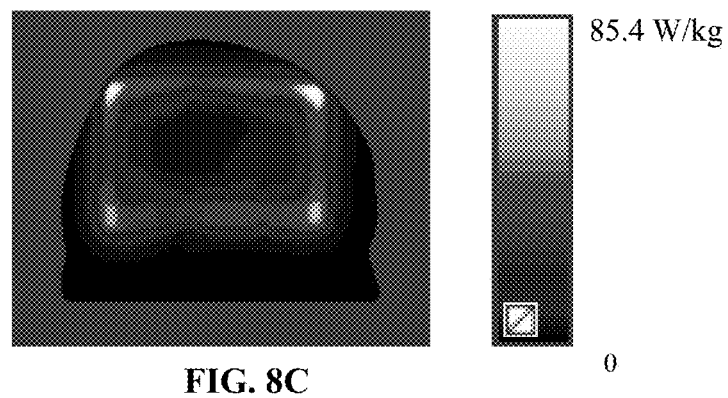

FIG. 8A-8C depict example simulation results of electric power absorbed by the tissue under the transducer array when electric fields are applied through transducers of different shapes to a subject's head. In the examples depicted in FIGS. 8A-8C, the transducers are conductive flexible sheets. In addition, the same TTFields with the same frequency and voltage are used to obtain the simulation results shown in FIGS. 8A-8C. FIGS. 8A-8C exhibit different instances of the edge effect.

In the example depicted in FIG. 8A, an oval shaped transducer is located on the subject's head to deliver the TTFields. As shown in FIG. 8A, the electric power delivered to the subject's head by the outer perimeter of the oval transducer is approximately 70 W/kg (yellow in color), and the electric power delivered by the center of the oval transducer is almost zero (black/dark blue in color). Additionally, the electric power delivered by the portions of the oval transducer between the center and the outer perimeter is approximately 12 W/kg (blue in color).

In the example depicted in FIG. 8B, a circular shaped transducer is located on the subject's head to deliver the TTFields. As shown in FIG. 8B, the electric power delivered to the subject's body by the outer perimeter of the circular transducer is approximately 50 W/kg (orange/yellow in color), and the electric power delivered by the center of the oval transducer is almost zero (black/dark blue in color). Additionally, the electric power delivered by the portions of the circular transducer between the center and the outer perimeter is approximately 12 W/kg (blue in color).

In the example depicted in FIG. 8C, a rectangle shaped transducer is located on the subject's head to deliver TTFields. As shown in FIG. 8C, the electric power delivered to the subject's body by the corners of the outer perimeter of the circular transducer is approximately 70 W/kg (yellow in color), and the electric power delivered by the edge of the outer perimeter is approximately 42 W/kg (red in color). Additionally, the electric power delivered by the center of the rectangle transducer is almost zero (black/dark blue in color), and the electric power delivered by the portions of the rectangle transducer between the center and the outer perimeter is approximately 12 W/kg (blue in color).

In comparison of the examples depicted in FIGS. 8A-8C, the electric power of the oval transducer (FIG. 8A) is distributed the most evenly around the outer perimeter of the transducer. Additionally, the electric power of the rectangle transducer (FIG. 8C) is distributed the least evenly around the outer perimeter of the transducer. Furthermore, the electric power of the circular transducer (FIG. 8B) is distributed less evenly around the outer perimeter of the transducer than the oval transducer, and more evenly than the rectangle transducer. In addition, the size of the center of the oval transducer where the electric power is almost zero is the smallest, the size of the center of the rectangle transducer is the largest, and the size of the center of the circular transducer is in-between the oval and the rectangle transducers.

Figure 9E:
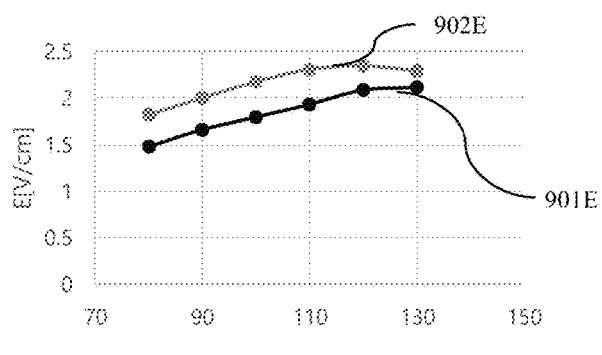

FIGS. 9A-9F depict example simulation results of electric field strength delivered to tumors as a function of the length of the rectangular transducer, in each case comparing the positioning of the transducer (a) such that the tumor is located centrally within the transducer array perimeter with (b) that of positioning the transducer such that the tumor is located at the edge of the transducer array perimeter. Each of FIGS. 9C-9F represent the relationship for different distances to the surface of the subject's head, with FIG. 9C showing the closest distance to the surface of the subject's head. As can be seen (9C), for near-surface tumors, the edge effect of the transducer can provide higher electric field strength.

FIG. 9A is an image of the side view of a three-dimensional model of a subject's head with a rectangular transducer located on the subject's head to deliver TTFields. In this example, the width of the rectangle transducer 903 is 65 mm. The length, L, of the rectangle transducer 903 varies from 80 mm to 130 mm (see x axis of the graphs in FIGS. 9C-9F). The image includes two tumor locations 901A and 902A, and each has four depth locations (which locations are, successively, 10 mm further from the surface), as can be seen in FIG. 9B.

FIG. 9B is a top view of the three-dimensional model of the subject's body of FIG. 9A showing eight tumor locations with four distances to the surface of the subject's head. Tumor locations 901A (FIG. 9A, right side of transducer) include locations 901-1B, 901-2B, 901-3B, and 901-4B (FIG. 9B, right side locations). Tumor locations 902A (FIG. 9A, center of transducer) include locations 902-1B, 902-2B, 902-3B, and 902-4B (FIG. 9B, left side locations). In the example depicted in FIG. 9B, the tumor locations 901-1B and 902-1B are closest to the surface of the subject's head (distance of 901-1B to surface=4 cm), the tumor locations 901-4B and 902-4B are furthest to the surface of the subject's head (distance of 901-4B to surface=7 cm), and the tumor locations 901-2B, 902-2B (distance of 901-2B to surface=5 cm), and 901-3B, 902-3B (distance of 901-3B to surface=6 cm) are in-between the tumor locations 901-1B and 902-1B and the tumor locations 901-4B and 902-4B. The transducer is located on the lower side of FIG. 9B, such that the locations 902-1B, 902-2B, 902-3B, and 902-4B in FIG. 9B line up behind the center of the transducer (as viewed in FIG. 9A), and the locations 901-1B, 901-2B, 901-3B, and 901-4B in FIG. 9B line up behind the right hand edge of the transducer (as viewed in FIG. 9A).

In view of FIGS. 9A and 9B, for tumor locations 901-1B to 901-4B, the simulation results are field strength delivered to the tumors by a portion of the outer perimeter of the transducer (corresponding to tumor locations 901A in FIG. 9A). Similarly, for tumor locations 902-1B to 902-4B, the simulation results are field strength delivered to the tumors by a central portion of the transducer (corresponding to tumor locations 902A in FIG. 9A).

FIG. 9C is a plot of the electric field strength delivered to tumor locations 901-1B and 902-1B as a function of the length of the transducer. In FIG. 9C, the plot 901C is the electric field strength delivered to tumor location 901-1B, that is with a portion of the outer perimeter of the transducer located at the near-tumor position on the subject's body, and the plot 902C is the electric field strength delivered to tumor location 902-1B, that is with a central portion of the transducer located at the near-tumor position on the subject's body. When the length of the transducer is equal to or less than 100 mm, the electric field strength of the outer perimeter and the central portion of the transducer are approximately the same. When the length of the transducer is greater than 100 mm, the electric field strength of the central portion of the transducer stays approximately the same while the electric field strength of the outer perimeter is increased greatly. As such, when a tumor is located with a distance to the surface of the subject's body equal to or less than the distance of location 1B to the surface of the subject's body, placing a portion of the outer perimeter of the transducer at the near-tumor position on the subject's head may deliver higher electric field power to the tumor.

FIG. 9D is a plot of the electric field strength delivered to tumor locations 901-2B and 902-2B as a function of the length of the transducer. In FIG. 9D, the plot 901D is the electric field strength delivered to tumor location 901-2B, that is with a portion of the outer perimeter of the transducer located at the near-tumor position on the subject's body, and the plot 902D is the electric field strength delivered to tumor location 902-2B, that is with a central portion of the transducer located at the near-tumor position on the subject's body. In the example depicted in FIG. 9D, the electric field strength of the outer perimeter and the central portion of the transducer are approximately the same. (Note: the y-axis scale in FIG. 9D differs from that in FIG. 9C). In addition, as the length of the transducer increases, the electric field strength of the portion of the outer perimeter increases, except when the length of the transducer is 100-120 mm. Additionally, when the length of the transducer increases, the electric field strength of the central portion of the transducer increases. As such, when a tumor is located with a distance to the surface of the subject's body equal to the distance of location 2B to the surface of the subject's body, either placing a portion of the outer perimeter of the transducer at the near-tumor position on the subject's head, or placing the central portion of the transducer at the near-tumor position on the subject's head may render similar electric field power to be delivered to the tumor.

FIG. 9E is a plot of the electric field strength delivered to tumor locations 901-3B and 902-3B as a function of the length of the transducer. In FIG. 9E, the plot 901E is the electric field strength delivered to tumor location 901-3B, that is with a portion of the outer perimeter of the transducer located at the near-tumor position on the subject's body, and the plot 902E is the electric field strength delivered to tumor location 902-3B, that is with a central portion of the transducer located at the near-tumor position on the subject's body. In the example depicted in FIG. 9E, the electric field strength of a portion of the outer perimeter of the transducer and that of the central portion of the transducer are approximately the same. (Note: the y-axis scale in FIGS. 9D, 9E, and 9F differs from that in FIG. 9C). In addition, as the length of the transducer increases, the electric field strength of the portion of the outer perimeter of the transducer and that of the central portion of the transducer increase. As such, when a tumor is located with a distance to the surface of the subject's body equal to the distance of location 3B to the surface of the subject's body, either placing a portion of the outer perimeter of the transducer at the near-tumor position on the subject's head, or placing the central portion of the transducer at the near-tumor position on the subject's head may render similar electric field power to be delivered to the tumor.

Figure 9F:
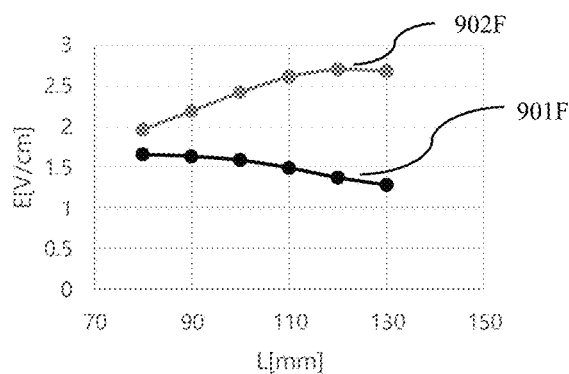

FIG. 9F is a plot of the electric field strength delivered to tumor locations 901-4B and 902-4B as a function of the length of the transducer. In FIG. 9F, the plot 901F is the electric field strength delivered to tumor location 901-4B, that is with a portion of the outer perimeter of the transducer located at the near-tumor position on the subject's body, and the plot 902F is the electric field strength delivered to tumor location 902-4B, that is with a central portion of the transducer located at the near-tumor position on the subject's body. In the example depicted in FIG. 9F, the electric field strength of a portion of the outer perimeter of the transducer is smaller than the electric field strength of the central portion of the transducer. In addition, as the length of the transducer increases, the electric field strength of the central portion of the transducer increases, while the electric field strength of the portion of the outer perimeter of the transducer decreases. As such, when a tumor is located with a distance to the surface of the subject's body equal to or greater than the distance of location 4B to the surface of the subject's body, placing the central portion of the transducer at the near-tumor position on the subject's head may deliver higher electric field power to the tumor.

In viewing FIGS. 9C-9F together, it should be noted that the y axis scale is somewhat different in FIG. 9C. Where the electric field strength data generally lies between 1.5-2.5 V/cm in FIGS. 9D-9F, the curve 901C in FIG. 9C shows a pronounced electric field strength of >6 V/cm for the edge-positioned transducer. That is, the most pronounced effect, by far, is seen for the edge-positioned transducer providing an electric field for the tumor at the location 901-1B which is the location closest to the surface of the body. However, the effect is only evident when the length of the transducer is 110 mm or greater. FIGS. 7A and 7B illustrate this effect qualitatively. FIG. 7A shows the shorter length transducer (L<110 mm) produces no edge effect—the charge is evenly distributed along the length of the transducer and there is no shorter route for current flow than through the center of the head. FIG. 7B, on the other hand, illustrates the case for a longer transducer (L>110 mm) which produces an edge effect—a greater concentration of charge is located at the edge of the transducer, and, moreover, there is a shorter route for current to flow from one transducer to another (from one edge to another) than through the center of the head. Accordingly, a larger electric field strength exists at the edge of the transducer for the longer transducer than for the shorter transducer.

Figure 10:
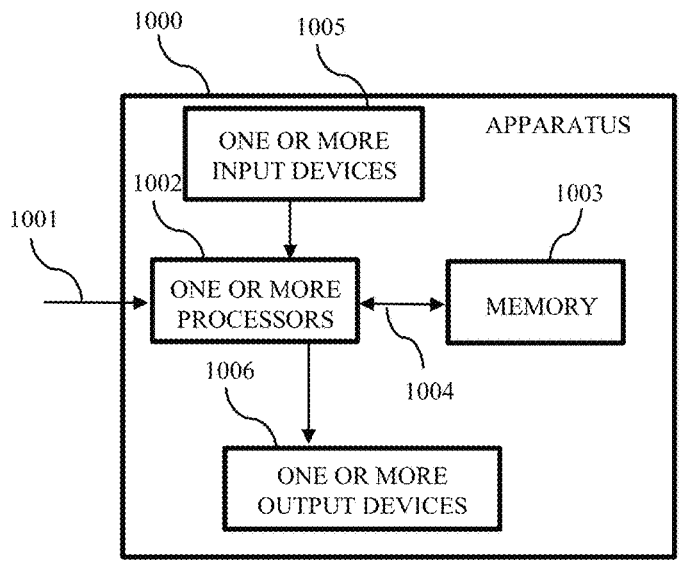
FIG. 10 depicts an example of an apparatus to generate a tumor segmentation with an uncertainty estimation of a subject's body.

FIG. 10 depicts an example of an apparatus 1000 to implement the methods discussed herein. In this example, the apparatus 1000 includes one or more processors 1002, one or more output devices 1006, a memory 1003, and one or more user input devices 1005.

The one or more processors 1002 may include a general-purpose processor, an integrated circuit, a server, other programmable logic device, or any combination thereof. The processor may be a conventional processor, microprocessor, controller, microcontroller, or state machine. The one or more processors may be one, two, or more processors of the same or different types. Furthermore, the one or more processors may be a computer, computing device and user device, and the like.

The memory 1003 is accessible by the one or more processors 1002 via the link 1004 so that the one or more processors 1002 can read information from and write information to the memory 1003. In one example, one or more user input collected by one or more user input devices 1005 is processed by the one or more processors 1002 and stored in the memory 1003. Memory may be integral with or separate from the processors. Examples of the memory 1003 include RAM, flash, ROM, EPROM, EEPROM, registers, disk storage, or any other form of storage medium. The memory 1003 may store instructions that when executed by the one or more processors 1002 implement, or cause the one or more processors 1002 to implement, one or more embodiments of the invention. Memory 1003 may be a non-transitory computer-readable medium that stores instructions, which when executed by a computer, cause the computer to perform one or more of the exemplary methods discussed herein In one example, based on one or more inputs 1001, the one or more processors select at least one of the plurality of portions of the outer perimeter and/or the plurality of orientations of the transducer for delivering tumor treating fields to the subject's body. The one or more inputs 1001 may include image data and/or user inputs. The one or more user inputs 1001 may be received via one or more input devices 1005. The selected at least one of the plurality of portions of the outer perimeter and/or the plurality of orientations may be output on the one or more output devices 1006 of the apparatus 1000.

ILLUSTRATIVE EMBODIMENTS

The invention includes other illustrative embodiments, such as the following.

Illustrative Embodiment 1. A computer-implemented method for determining a location of a transducer on a subject's body for applying tumor treating fields, the method comprising: determining a near-surface portion of a tumor in the subject's body, the near-surface portion of the tumor closer to a surface of the subject's body than other portions of the tumor; determining a near-tumor position on the subject's body, the near-tumor position on the subject's body closer to the near-surface portion of the tumor than other positions of the subject's body; determining, for a first transducer of a pair of transducers to be located on the subject's body for applying tumor treating fields, an outer perimeter of the first transducer, the first transducer comprising a plurality of electrode elements electrically coupled to each other, the plurality of electrode elements of the first transducer being located within the outer perimeter; and identifying a portion of the outer perimeter of the first transducer to be located substantially at the near-tumor position on the subject's body.

Illustrative Embodiment 2. The method of Illustrative Embodiment 1, wherein the near-surface portion of the tumor is less than or equal to 80 mm from the near-tumor position on the subject's body.

Illustrative Embodiment 3. The method of Illustrative Embodiment 2, wherein the near-surface portion of the tumor is less than or equal to 66 mm from the near-tumor position on the subject's body.

Illustrative Embodiment 4. The method of Illustrative Embodiment 2, further comprising: determining a central portion of the first transducer located centrally within the outer perimeter of the first transducer; determining a power density at the portion of the outer perimeter of the first transducer and a power density at the central portion of the first transducer when applying tumor treating field to the subject's body, wherein the power density at the portion of the outer perimeter of the first transducer is 100% to 300% of the power density at the central portion of the first transducer.

Illustrative Embodiment 5. The method of Illustrative Embodiment 1, wherein, for a line segment having first and second end points on opposite sides of the subject's body and intersecting the near-surface portion of the tumor, the first end point intersecting the near-tumor position on the subject's body, a distance between the first end point and the near-surface portion of the tumor is equal to or less than 50% of a distance between the second end point and the near-surface portion of the tumor.

Illustrative Embodiment 6. The method of Illustrative Embodiment 5, wherein the distance between the first end point and the near-surface portion of the tumor is equal to or less than 25% of the distance between the second end point and the near-surface portion of the tumor.

Illustrative Embodiment 7. The method of Illustrative Embodiment 1, wherein a surface area of the first transducer is equal to or greater than 5000 mm$^2$.

Illustrative Embodiment 8. The method of Illustrative Embodiment 1, wherein a surface area of the first transducer is equal to or greater than 6500 mm$^2$.

Illustrative Embodiment 9. The method of Illustrative Embodiment 1, wherein the first transducer is configured to be positioned over the subject's body with a face of the first transducer facing the subject's body; wherein, when viewed from a direction perpendicular to the face of the first transducer, the near-surface portion of the tumor is substantially within the outer perimeter of the first transducer.

Illustrative Embodiment 10. The method of Illustrative Embodiment 1, wherein the near-tumor position on the subject's body is substantially within the outer perimeter of the first transducer and is located at a distance from the outer perimeter that is less than 10% of the distance from the outer perimeter to the centroid of the transducer.

Illustrative Embodiment 11. The method of Illustrative Embodiment 1, wherein the near-tumor position on the subject's body is substantially within the outer perimeter of the first transducer and is located at a distance from the outer perimeter that is from 0% to 50% of the distance from the outer perimeter to the centroid of the transducer.

Illustrative Embodiment 12. The method of Illustrative Embodiment 1, wherein the first transducer is configured to be positioned over the subject's body with a face of the first transducer facing the subject's body; wherein, when viewed from a direction perpendicular to the face of the first transducer, a number of the electrode elements of the first transducer are peripheral electrode elements defining the outer perimeter of the first transducer, the peripheral electrode elements substantially surrounding any other electrode elements of the first transducer.

Illustrative Embodiment 13. The method of Illustrative Embodiment 1, wherein at least one of the electrode elements of the first transducer touches the portion of the outer perimeter of the first transducer to be located substantially at the near-tumor position on the subject's body.

Illustrative Embodiment 14. The method of Illustrative Embodiment 1, wherein the portion of the outer perimeter of the first transducer to be located substantially at the near-tumor position on the subject's body is 20% or less of the outer perimeter.

Illustrative Embodiment 15. The method of Illustrative Embodiment 14, wherein the portion of the outer perimeter of the first transducer to be located substantially at the near-tumor position on the subject's body is 10% or less of the outer perimeter.

Illustrative Embodiment 16. The method of Illustrative Embodiment 1, wherein the outer perimeter of the first transducer is substantially square, rectangular, regular polygonal, irregular polygonal, circular, oval, ovaloid, ovoid, or elliptical in shape.

Illustrative Embodiment 17. The method of Illustrative Embodiment 1, further comprising: identifying a plurality of portions of the outer perimeter of the first transducer to be located substantially at the near-tumor position on the subject's body; selecting at least one of the plurality of portions of the outer perimeter of the first transducer; and outputting the selected at least one of the plurality of portions of the outer perimeter of the first transducer to determine the location of the transducer on a subject's body for applying tumor treating fields.

Illustrative Embodiment 18. The method of Illustrative Embodiment 1, further comprising: identifying a plurality of orientations of the first transducer on the subject's body to substantially locate the portion of the outer perimeter of the first transducer at the near-tumor position on the subject's body; selecting at least one of the plurality of orientations of the first transducer; and outputting the selected at least one of the plurality of orientations of the first transducer to determine the location of the transducer on a subject's body for applying tumor treating fields.

Illustrative Embodiment 19. The method of Illustrative Embodiment 1, wherein the electrode elements are capacitively coupled.

Illustrative Embodiment 20. The method of Illustrative Embodiment 1, wherein the electrode elements are not capacitively coupled.

Illustrative Embodiment 21. The method of Illustrative Embodiment 1, wherein the electrode elements comprise polymer films.

Illustrative Embodiment 22. The method of Illustrative Embodiment 1, wherein the electrode elements comprise ceramic disks.

Illustrative Embodiment 23. The method of Illustrative Embodiment 1, wherein the tumor is located in a head of the subject's body.

Illustrative Embodiment 24. The method of Illustrative Embodiment 1, wherein the tumor is located in a torso of the subject's body.

Illustrative Embodiment 25. A computer-implemented method for determining a location of a transducer on a subject's body for applying tumor treating fields, the method comprising: determining, for a first transducer of a pair of transducers to be located on the subject's body for applying tumor treating fields, an edge of the first transducer, the first transducer comprising an array of electrode elements electrically coupled to each other; determining a near-surface location of a tumor in the subject's body and a closest near-tumor position on a surface of the subject's body; and identifying, when viewed from a direction perpendicular to a face of the first transducer to be positioned over the subject's body, a segment of the edge of the first transducer that substantially overlaps the near-surface location of tumor, the segment of the edge being closer to the near-tumor position on the surface of the subject's body than a centroid of the first transducer.

Illustrative Embodiment 26. The method of Illustrative Embodiment 25, wherein, when viewed from the direction perpendicular to the face of the first transducer, the near-tumor position on the surface of the subject's body is located at a distance from the edge of the transducer that is less than 10% of the distance from the edge of the transducer to the centroid of the transducer.

Illustrative Embodiment 27. The method of Illustrative Embodiment 25, wherein, when viewed from the direction perpendicular to the face of the first transducer, the near-tumor position on the surface of the subject's body is located at a distance from the edge of the transducer that is from 0% to 50% of the distance from the edge of the transducer to the centroid of the transducer.

Illustrative Embodiment 28. The method of Illustrative Embodiment 25, wherein, when viewed from the direction perpendicular to the face of the first transducer, a number of the electrode elements are peripheral electrode elements defining the edge of the first transducer, the peripheral electrode elements substantially surrounding any other electrode elements of the first transducer.

Illustrative Embodiment 29. An apparatus for determining a location of a transducer on a subject's body for applying tumor treating fields, the apparatus comprising: one or more processors; and memory accessible by the one or more processors, the memory storing instructions that when executed by the one or more processors, cause the apparatus to: determine, for a first transducer of a pair of transducers to be located on the subject's body for applying tumor treating fields, a convex periphery of the first transducer, the first transducer comprising an array of electrode elements electrically coupled to each other, the convex periphery surrounding all of the electrode elements of the first transducer, the convex periphery touching at least three of the electrode elements; determine a near-surface location of a tumor in the subject's body, the near-surface location of the tumor closer to a surface of the subject's body than other locations of the tumor; and identify a near-tumor portion of the convex periphery of the first transducer to be located on the subject's body closer to the near-surface location of the tumor than other portions of the first transducer.

Illustrative Embodiment 30. A method of applying tumor treating fields to a subject's body having a tumor, the method comprising: locating a first pair of transducers on the subject's body and a second pair of transducers on the subject's body; and alternately applying a first electric field between the first pair of transducers and a second electric field between the second pair of transducers; wherein a first transducer of the first pair of transducers is configured to be positioned over the subject's body with a face of the first transducer facing the subject's body, wherein the first transducer has a plurality of electrode elements electrically coupled to each other, wherein, when viewed from a direction perpendicular to the face of the first transducer, a number of the electrode elements of the first transducer are peripheral electrode elements defining a convex outer perimeter of the first transducer, the peripheral electrode elements substantially surrounding any other electrode elements of the first transducer, wherein the tumor has a near-surface portion of the tumor located closer to a near-tumor position on a surface of the subject's body than other portions of the tumor, and wherein a near-tumor portion of the convex outer perimeter of the first transducer is located closer to the near-surface portion of the tumor than other portions of the first transducer.

Illustrative Embodiment 31. The method of Illustrative Embodiment 30, wherein the first transducer is positioned such that the near-tumor position on the surface of the subject's body is substantially within the outer perimeter of the first transducer and is located at a distance from the outer perimeter that is less than 10% of the distance from the outer perimeter to the centroid of the transducer.

Illustrative Embodiment 32. The method of Illustrative Embodiment 30, wherein the first transducer is positioned such that the near-tumor position on the surface of the subject's body is substantially within the outer perimeter of the first transducer and is located at a distance from the outer perimeter that is from 0% to 50% of the distance from the outer perimeter to the centroid of the transducer.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A computer-implemented method for determining a location of a transducer on a subject's body for applying tumor treating fields, the method comprising:
   determining a near-surface portion of a tumor in the subject's body, the near-surface portion of the tumor closer to a surface of the subject's body than other portions of the tumor;
   determining a near-tumor position on the subject's body, the near-tumor position on the subject's body closer to the near-surface portion of the tumor than other positions of the subject's body;
   determining, for a first transducer of a pair of transducers to be located on the subject's body for applying tumor treating fields, an outer perimeter of the first transducer, the first transducer comprising a plurality of electrode elements electrically coupled to each other, the plurality of electrode elements of the first transducer being located within the outer perimeter; and
   identifying a portion of the outer perimeter of the first transducer to be located substantially at the near-tumor position on the subject's body.

2. The method of claim 1, wherein the near-surface portion of the tumor is less than or equal to 80 mm from the near-tumor position on the subject's body.

3. The method of claim 2, further comprising:
   determining a central portion of the first transducer located centrally within the outer perimeter of the first transducer;
   determining a power density at the portion of the outer perimeter of the first transducer and a power density at the central portion of the first transducer when applying tumor treating field to the subject's body,
   wherein the power density at the portion of the outer perimeter of the first transducer is 100% to 300% of the power density at the central portion of the first transducer.

4. The method of claim 1, wherein, for a line segment having first and second end points on opposite sides of the subject's body and intersecting the near-surface portion of the tumor, the first end point intersecting the near-tumor position on the subject's body, a distance between the first end point and the near-surface portion of the tumor is equal to or less than 50% of a distance between the second end point and the near-surface portion of the tumor.

5. The method of claim 1, wherein a surface area of the first transducer is equal to or greater than 5000 mm$^2$.

6. The method of claim 1, wherein the first transducer is configured to be positioned over the subject's body with a face of the first transducer facing the subject's body;
   wherein, when viewed from a direction perpendicular to the face of the first transducer, the near-surface portion of the tumor is substantially within the outer perimeter of the first transducer.

7. The method of claim 1, wherein the near-tumor position on the subject's body is substantially within the outer perimeter of the first transducer and is located at a distance from the outer perimeter that is from 0% to 50% of the distance from the outer perimeter to the centroid of the transducer.

8. The method of claim 1, wherein the first transducer is configured to be positioned over the subject's body with a face of the first transducer facing the subject's body;

wherein, when viewed from a direction perpendicular to the face of the first transducer, a number of the electrode elements of the first transducer are peripheral electrode elements defining the outer perimeter of the first transducer, the peripheral electrode elements substantially surrounding any other electrode elements of the first transducer.

9. The method of claim 1, wherein at least one of the electrode elements of the first transducer touches the portion of the outer perimeter of the first transducer to be located substantially at the near-tumor position on the subject's body.

10. The method of claim 1, wherein the portion of the outer perimeter of the first transducer to be located substantially at the near-tumor position on the subject's body is 20% or less of the outer perimeter.

11. The method of claim 1, wherein the outer perimeter of the first transducer is substantially square, rectangular, regular polygonal, irregular polygonal, circular, oval, ovaloid, ovoid, or elliptical in shape.

12. The method of claim 1, further comprising:
identifying a plurality of portions of the outer perimeter of the first transducer to be located substantially at the near-tumor position on the subject's body;
selecting at least one of the plurality of portions of the outer perimeter of the first transducer; and
outputting the selected at least one of the plurality of portions of the outer perimeter of the first transducer to determine the location of the transducer on a subject's body for applying tumor treating fields.

13. The method of claim 1, further comprising:
identifying a plurality of orientations of the first transducer on the subject's body to substantially locate the portion of the outer perimeter of the first transducer at the near-tumor position on the subject's body;
selecting at least one of the plurality of orientations of the first transducer; and
outputting the selected at least one of the plurality of orientations of the first transducer to determine the location of the transducer on a subject's body for applying tumor treating fields.

14. The method of claim 1, wherein the electrode elements are capacitively coupled.

15. The method of claim 1, wherein the tumor is located in a head of the subject's body.

16. The method of claim 1, wherein the tumor is located in a torso of the subject's body.

17. A computer-implemented method for determining a location of a transducer on a subject's body for applying tumor treating fields, the method comprising:
determining, for a first transducer of a pair of transducers to be located on the subject's body for applying tumor treating fields, an edge of the first transducer, the first transducer comprising an array of electrode elements electrically coupled to each other;
determining a near-surface location of a tumor in the subject's body and a closest near-tumor position on a surface of the subject's body; and
identifying, when viewed from a direction perpendicular to a face of the first transducer to be positioned over the subject's body, a segment of the edge of the first transducer that substantially overlaps the near-surface location of tumor, the segment of the edge being closer to the near-tumor position on the surface of the subject's body than a centroid of the first transducer.

18. The method of claim 17, wherein, when viewed from the direction perpendicular to the face of the first transducer, the near-tumor position on the surface of the subject's body is located at a distance from the edge of the transducer that is from 0% to 50% of the distance from the edge of the transducer to the centroid of the transducer.

* * * * *